(12) United States Patent
Zhu et al.

(10) Patent No.: US 9,617,487 B2
(45) Date of Patent: Apr. 11, 2017

(54) PROCESS FOR RESOURCING MUNICIPAL SOLID WASTE

(71) Applicants: Zuolin Zhu, San Diego, CA (US); Jonathan Zhu, San Diego, CA (US)

(72) Inventors: Zuolin Zhu, San Diego, CA (US); Jonathan Zhu, San Diego, CA (US)

( * ) Notice: Subject to any disclaimer, the term of this patent is extended or adjusted under 35 U.S.C. 154(b) by 14 days.

(21) Appl. No.: 14/492,304

(22) Filed: Sep. 22, 2014

(65) Prior Publication Data

US 2016/0083663 A1 Mar. 24, 2016

(51) Int. Cl.
| | | |
|---|---|---|
| C10L 1/00 | (2006.01) | |
| C10L 1/02 | (2006.01) | |
| C07C 51/09 | (2006.01) | |
| C07C 67/00 | (2006.01) | |
| C07C 27/00 | (2006.01) | |
| C10G 29/20 | (2006.01) | |
| C10G 31/09 | (2006.01) | |
| C10G 57/00 | (2006.01) | |
| C10G 1/00 | (2006.01) | |
| C10G 1/08 | (2006.01) | |
| C10G 1/10 | (2006.01) | |

(52) U.S. Cl.
CPC ............... *C10L 1/02* (2013.01); *C07C 27/00* (2013.01); *C07C 51/09* (2013.01); *C07C 67/00* (2013.01); *C10G 1/002* (2013.01); *C10G 1/08* (2013.01); *C10G 1/086* (2013.01); *C10G 1/10* (2013.01); *C10G 29/205* (2013.01); *C10G 31/09* (2013.01); *C10G 57/005* (2013.01); *C10L 2200/0469* (2013.01); *C10L 2290/02* (2013.01); *C10L 2290/547* (2013.01)

(58) Field of Classification Search
CPC ............... C10L 1/02; C10L 2200/0469; C10L 2290/547; C07C 51/09; C07C 67/035
See application file for complete search history.

(56) References Cited

U.S. PATENT DOCUMENTS

| | | | | |
|---|---|---|---|---|
| 4,094,740 A * | 6/1978 | Lang | ...................... | A23K 1/003 127/36 |
| 7,771,699 B2 * | 8/2010 | Adams et al. | ........... | C10G 1/02 422/198 |
| 7,811,456 B2 * | 10/2010 | Choate et al. | ........... | B09B 3/00 210/603 |
| 7,964,761 B2 * | 6/2011 | Zmierczak et al. | ... | C10G 1/002 44/605 |
| 9,181,166 B1 * | 11/2015 | Zhu | ......................... | C07C 51/00 |
| 2003/0100807 A1 * | 5/2003 | Shabtai | ................. | C10G 45/02 585/240 |
| 2011/0180752 A1 * | 7/2011 | Zhu | ......................... | C10G 1/06 252/182.31 |

\* cited by examiner

Primary Examiner — Cephia D Toomer

(57) ABSTRACT

A process for converting organic MSW into liquid fuels or chemical products in almost quantitative yield via catalytic one-pot hydrolytic depolymerization of organic MSW. The organic MSW comprises all organic materials that exists in municipal solid waste, such as paper and paperboard, food scraps, yard trimmings, rubber, leather, textiles, wood, plastics, etc. The process is the first one over the world for resourcing municipal solid waste.

10 Claims, 3 Drawing Sheets

PROCESS FOR RESOURCING MUNICIPAL SOLID WASTE

FIELD OF THE INVENTION

The present invention is related to a novel process for resourcing municipal solid waste. More specifically, the present invention is related to a process for refining organic components of municipal solid waste into liquid fuels or organic chemical products in an almost quantitative yield.

DESCRIPTION OF RELATED ART

The percentage of organic components in municipal solid waste (MSW) is high in developed countries: generally above 60% and even higher than 80% (83% for USA, 2009 EPA data, Table 1). The composition materials of MSW, such as paper and paperboard, food scraps, yard trimmings, plastics, rubber, leather, textiles, and wood, are organic materials. In developing countries, the percentage of organic components in MSW is about 50%. Thus, MSW is a potentially important resource of organic carbons.

TABLE 1

| MSW Composition, USA, 2009 | | |
|---|---|---|
| Component name | Percentage (%) | Remarks |
| Paper and Paperboard | 28.2 | Cellulose, with little lignin and hemicellulose |
| Food Scraps | 14.1 | Starch, fat or oil, protein, sugar, DNA, RNA |
| Yard Trimmings | 13.7 | Cellulose, lignin, hemicellulose, wax |
| Plastics | 12.3 | Polyesters, polyacrylates, silicones, polyurethanes, halogenated polyenes |
| Metals | 8.6 | Inorganic materials |
| Rubber, Leather, Textiles | 8.3 | Polyisopropene, protein, cellulose |
| Wood | 6.5 | Cellulose, lignin, hemicellulose |
| Glass | 4.8 | Inorganic materials |
| Other | 3.5 | Mostly inorganic materials |

There are no cost-effective technologies available for refining organic MSW. Current methods for MSW treatment, such as landfill or combustion, not only waste organic materials, but also require excess spending costs. The landfill method of MSW contaminates land and underground water. Methane formed during the decay of organic materials is a more powerful green house gas than carbon dioxide. The combustion method for organic MSW will generate toxic volatile gases such as nitrogen oxides and sulfur oxides, due to the existence of proteins and other organic sulfurs and nitrogen chemicals. Complete removal of these toxic gases from emission is expensive. MSW combustion cannot produce any organic chemical products, and the electricity price from MSW combustion is much higher than that from coal combustion. Many chemicals that exist in MSW are poisons for all known conventional catalysts, resulting in a lack of a method for selectively converting organic MSW into a few chemical products. Due to the complexity of MSW, sorting all of its organic components is too expensive and difficult.

Although there are many R&D projects for resourcing MSW, recycling has become the only effective one. Thus, the majority of components of organic MSW are still being wasted. All methods that have been developed from the modification of petro-chemical processes or coal chemical processes are commercially impractical due to their high costs of operation. For example, the pyrolysis of organic MSW shows no selectivity for any product, and the process is highly corrosive. The product is a mixture of phenols, aldehydes, alcohols, acids, alkanes, olefins, esters, ethers, etc. The formation of black tar and gasification is always observed in large amounts, thus the process gives very low yields of liquid products.

In summary, all the existing methods for treating municipal solid waste are not only unprofitable, but also wasteful of one of the most important resources of organic materials.

SUMMARY OF THE INVENTION

It is a primary object of the present invention to provide a novel cost-effective process for resourcing municipal solid waste. The products from resourcing municipal solid waste should be produced and supplied in large quantities, such as liquid fuels, at competitive prices.

It is a another object of the present invention to provide a catalytic system for the one-pot hydrolytic depolymerization reaction of all organic materials of municipal solid waste with the highest selectivity for liquid products. The catalytic system should be able to tolerate all kinds of chemicals that are poisons for known conventional catalysts. Municipal solid waste may contain: all kinds of heavy metals, inorganic and organic sulfur chemicals, inorganic and organic nitrogen chemicals, etc. These chemicals are known poisons for conventional catalysts.

It is another object of the present invention to provide a refining process, in which there will be neither black tar formation nor gasification during the one-pot hydrolytic depolymerization reaction catalyzed by the novel catalysts. A high percentage of conversion from organic MSW to products is crucial for economically resourcing municipal solid waste.

It is another object of the present invention to provide a refining process, in which the isolation and separation of products require only one step of operation. The process should be able to tolerate high ash content due to the nature of municipal solid waste. A high percentage of product isolation yield for the catalytic hydrolytic depolymerization is also crucial for resourcing municipal solid waste.

It is a key object of the present invention to provide a process for producing liquid fuels and fine chemicals which are reliable and cost-effective. "Cost-effective" means that the manufacturing costs of the products from MSW are comparable or even lower than that of petro-chemical processes.

To achieve the foregoing objects, and in accordance with the invention as embodied and described herein, a novel catalytic system and a method of product isolation are provided for resourcing municipal solid waste.

DETAILED DESCRIPTION OF THE INVENTION

Figure 1:
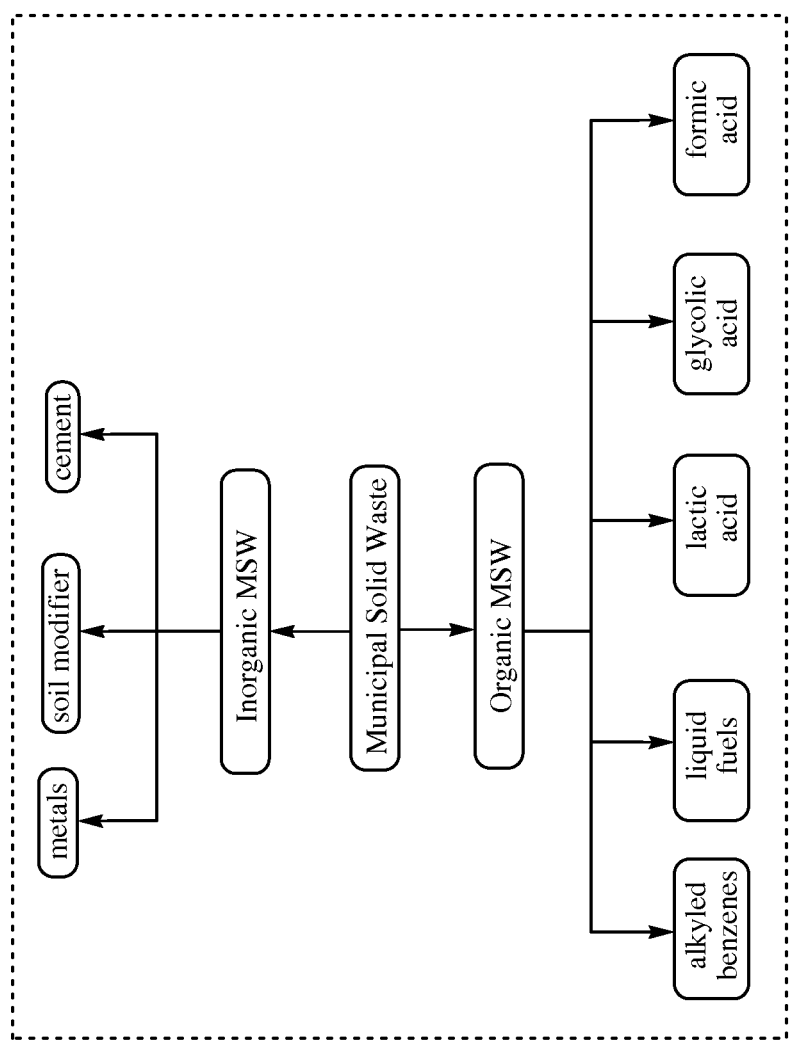
FIG. 1 illustrates the scheme for resourcing municipal solid waste.

The present invention is directed to a novel process for resourcing municipal solid waste. MSW can be transformed into a series of products in high yield using this invented process. The process is simple and easy to operate as shown by FIG. 1. Organic materials of MSW will be converted into alkylated benzenes, high quality liquid fuels, organic acids such as lactic acid and glycolic acid, etc. These products are currently made from fossil petroleum oil or grains. The inorganic materials of MSW will be converted into metals, soil modifier, cement, etc.

The present invention provides a novel catalytic system for the catalytic one-pot hydrolytic depolymerization of all organic materials of municipal solid waste. The catalytic system is capable of tolerating all kinds of chemicals that are poisons for known conventional catalysts. The catalysts are organic chemicals shown by Formula I and Formula II.

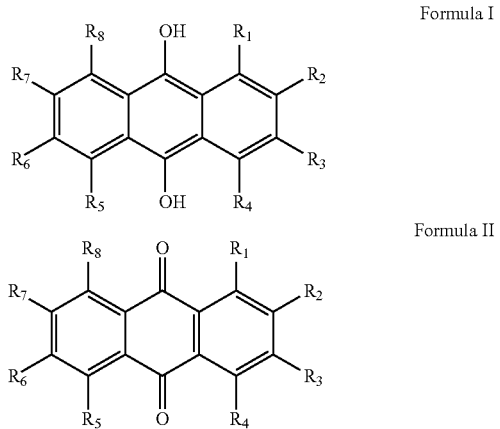

In formula I and formula II, $R_1$, $R_2$, $R_3$, $R_4$, $R_5$, $R_6$, $R_7$, and $R_8$ can be the same or different. They can be H, $SO_3H$, $NO_2$, $NH_2$ and OH (for example, if they are all H, the chemical is anthraquinone for Formula II; and 9,10-dihydoxyanthracene for Formula I). $R_1$, $R_2$, $R_3$, $R_4$, $R_5$, $R_6$, $R_7$, and $R_8$ cannot be all other groups such as halides, alkyls, carbonyls, carboxylics, etc., because these groups will breakdown, resulting in the degradation of the catalyst due to the nature of municipal solid waste.

The present invention provides a novel catalytic system for the catalytic one-pot hydrolytic depolymerization of all organic materials of municipal solid waste. The aromatic products, obtained from catalytic one-pot hydrolytic depolymerization of all organic materials of municipal solid waste, is also good catalyst for the reaction.

The present invention provides a novel cost-effective process for converting organic MSW into small organic molecules in an almost quantitative yield. There is only one reaction step for the catalytic one-pot hydrolytic depolymerization of all organic materials of MSW into small organic molecules with high product selectivity. "High product selectivity" means that there are only two kinds of organic products: small molecular aromatics and small organic acids. Small organic acids include fat acids, formic acid, acetic acid, glycolic acid, lactic acid, etc. The isolation and separation of these two products also only require one step of operation. The process of the invention provides the basis for a cost-effective manufacturing technology aimed at resourcing municipal solid waste.

The present invention is directed to a two-step process for converting all kinds of organic MSW into small organic molecules. It is a novel process with the potential to be economically practical for resourcing municipal solid waste.

As fossil petroleum is expected to continue to play a predominant role in providing organic products in the near future, organic products from resourcing municipal solid waste should be produced and supplied in large quantities and at competitive prices.

Figure 2:
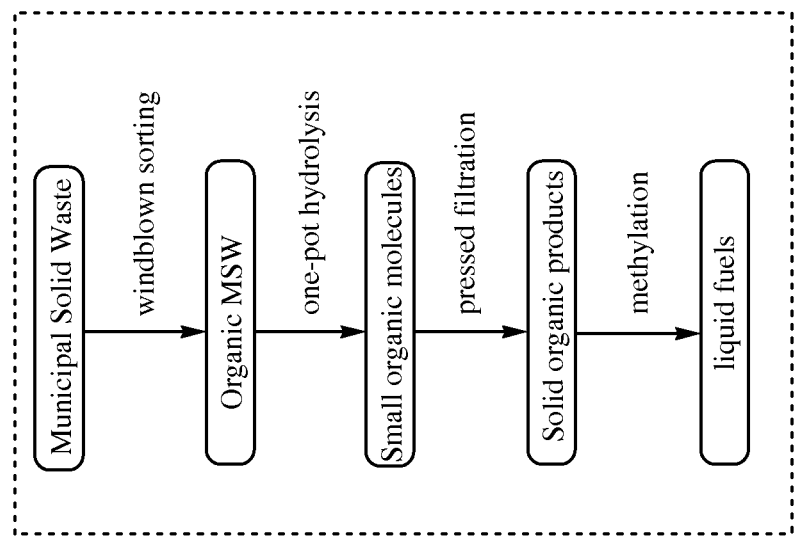
FIG. 2 illustrates the invented process for converting organic MSW into liquid fuels.

In the first step of the process of the invention, as described in FIG. 2, municipal solid waste is subjected to wind-blown sorting. Organic materials of MSW are isolated using the density differences between them and metals, ash, moisture, etc. Ash content of the isolated organic MSW is below 30%.

In the second step of the process of the invention, organic MSW is subjected to a catalytic one-step hydrolytic depolymerization in a one-pot reaction. All organic materials of MSW, such as paper and paperboard, food scraps, yard trimmings, polyesters and polyether of plastics and rubbers, leather, textiles, wood, etc., are depolymerized into two kinds of small organic molecules. The reaction is fast with good product selectivity; neither gasification nor black tar formation is observed during the catalytic one-step hydrolytic depolymerization reaction.

Oxides or hydroxides of alkaline earth metals are added into the catalytic one-pot hydrolytic depolymerization to facilitate the one step isolation and separation. It is almost impossible to fulfill the one step isolation and separation process without the use of oxides or hydroxides of alkaline earth metals.

The metals in oxides or hydroxides are alkaline earth metals and transition metals. The simple rule for the selection of the metals is the availability and the prices of the oxides or hydroxides. For example, when the MSW refining facility is near a steel manufacturing plant, iron(II) oxide is preferred, because slag is easy to obtain and reasonably priced. When the MSW refining facility is near a lime production plant or located in an area where limestone resource is very rich, calcium oxide or calcium hydroxide is preferred.

The ratio of organic materials to oxide or hydroxide depends on the nature of organic MSW. In principal, the higher the content of lignin, the lower the amount of oxide or hydroxide needed. For example, when organic MSW has a lignin content less than 10%, the catalytic one-step hydrolytic depolymerization of 50 grams of organic MSW requires a one molar equivalent of hydroxide anion. When organic MSW has a lignin content higher than 30%, a one molar equivalent of hydroxide anion can fulfill the completed hydrolytic depolymerization of 100 grams of organic MSW. The requirement of metal oxide or hydroxide for the completed catalytic one-pot hydrolytic depolymerization of organic MSW, expressed as the one molar equivalent of hydroxide anion, is in the range of 50 grams of organic MSW/one molar equivalent of hydroxide anion to 100 grams of organic MSW/one molar equivalent of hydroxide anion.

In the third step of the process of the invention, as described in FIG. 2, products are isolated and separated by filtration. In the present invention, there are only two kinds of products obtained from the catalytic one-pot hydrolytic depolymerization of organic MSW: small molecular aromatics and small organic acids. Small organic acids include fat acids, formic acid, acetic acid, glycolic acid, lactic acid, etc. With the help of alkaline earth metal oxides or hydroxides, when the temperature of the product solution is controlled below ten degrees Celsius, all organic products are almost insoluble in water. Pressed filtration is preferred for product isolation, so the water content of the solid products can be lower than 40%, or even lower than 30%.

According to the invention, the isolated products of organic molecules can be converted into high quality liquid fuels using a one step reaction. Alkylation with dimethyl sulfate or dimethyl carbonate is the preferred method. The required amount of methylation reagent for the organic MSW with lignin content is 30% by weight—0.6 mole of methylation reagent is needed for alkylating 100 grams of organic product. The required amount of methylation reagent for the organic MSW with lignin content is 10% by weight—0.8 mole of methylation reagent is needed for alkylating 100 grams of organic product.

According to the invention, the liquid fuels from the methylation reaction can be separated into aromatic chemicals and non-aromatic chemicals via water extraction. All the esters of lactic acid, formic acid, glycolic acid, and acetic acid are extracted into an aqueous phase. Separation of these isolated aromatic chemicals into pure single compound, and esters into pure lactate, glycolate, acetate, formate, can be fulfilled via a distillation method.

The following examples are included to demonstrate the preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Analysis and separation of organic acids: The organic acids are analyzed using the following methods and conditions: HPLC, Agilent 1200, column: SB-AQ, 5 μm, 4.60× 250 mm; mobile phase: 0.025M, pH=2.5 phosphate buffer solution, flow rate: 0.6 ml/min for 0-10 min, 0.6 ml/min to 1.2 ml/min from 10-15 min, 1.2 ml/min to 0.6 ml/min from 15-30 min, then at 0.6 ml/min for 45 minutes. A DAD detector is used at wavelength 210 nm and a column temperature is kept at 30° C. Sample size is 5 μl and all organic acids have a retention time of less than 14 minutes.

All volatile products such as phenols are analyzed using GCMS: Agilent 7890 GC with Agilent 5975C MS; Column: DB-5, 30 m×0.25 mm×0.25 μm; Injector: 10:1 split, 250° C.; Carrier gas: helium at 1.0 ml/min; Temperature: 60° C. initial, hold 5 min, ramp at 2° C./min to 200° C., hold 5 min, ramp at 2° C./min to 280° C., hold 5 min; Detector: Agilent 5975C; transfer line temperature 280° C.; ion source temperature 230° C.; quadruple temperature 150° C.; mass range 40-500 ug; ionization voltage 70 ev; Injection volume 0.2 μl.

| Molecular mass of small molecular aromatics: | Source Type: APCI |
| --- | --- |
| APCI Vaporizer Temp (° C.): 500.00 | Sheath Gas Flow (arb): 50.00 |
| Aux Gas Flow (arb): 10.00 | Sweep Gas Flow (arb): 5.00 |
| Capillary Temp (° C.): 350.00 | I Spray voltage(kv): 3.5 |
| Capillary voltage (v): −31 | Tube lens (V): −90 |

Example 1

Samples of organic MSW are prepared according to EPA data as shown in Table 1. All components are calculated as dried materials. Through the variation of the quantities of brown paperboard, pine needles, and wood, two kinds of organic MSW are prepared. One of them contains 10% lignin (Organic MSW A), and another contains 30% lignin (Organic MSW B).

| Component name | Percentage (%) |
| --- | --- |
| Paper, Paperboard | 34 |
| Bread, noodle, fat and vegetable oil, rice, tomato, and potato | 17 |
| Wild grass, tree branches, pine needles, and flowers | 16.5 |
| Polyester and polyether plastic | 14.8 |
| Leather, cotton cloths | 10 |
| Wood | 7.8 |

To a 1 liter stainless steel autoclave equipped with mechanical stirrer, add 750 ml of distilled water, 112 g of dried organic MSW B, 42 g of calcium oxide, and 1 g of 9,10-dihydroxyanthracene. The autoclave is sealed, purged with nitrogen three times, then filled with nitrogen at a pressure of 0.2-1 MPa, heated to 180° C. and maintain at this temperature for ten minutes. The temperature is then increased to 250° C. and stirred at this temperature for 50 min. After cooling to a temperature below 50° C., a brown color liquid mixture is obtained (the color slowly turns deeper after the mixture is exposed to air). The liquid mixture is then cooled down to a temperature below 10 degrees Celsius with stirring. Pressed filtration is carried out with the temperature maintained below 10 degrees Celsius. The brown color solid product obtained is 215 grams with 28% of water content. The yield is 100% based on the organic MSW.

Figure 3:
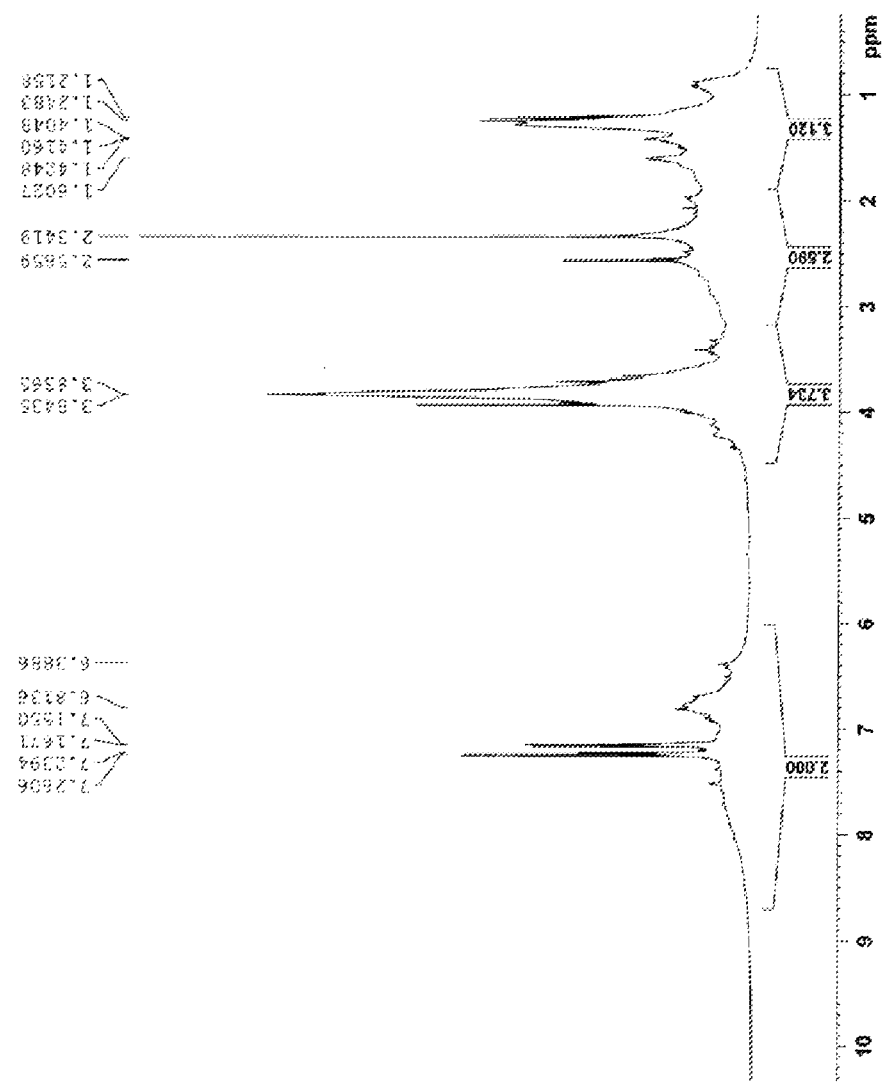
FIG. 3 illustrates the $^1$H-NMR of the aromatic liquid. The ratio of aliphatic hydrogen to aromatic hydrogen is 4.8:1.

The brown color solid is dried under vacuum with a temperature controlled below 60 degrees Celsius, then suspended in 1000 ml of anhydrous methanol, 100 g of dimethyl carbonate is added to the mixture. The mixture is sealed inside a 2 liter stainless steel autoclave equipped with mechanical stirrer. The reaction mixture is then heated to 180 degrees Celsius with vigorous stirring. After a two hour reaction, the reaction mixture is cooled down to room temperature. Pressed filtration is carried out to remove all solids. Products are isolated using distillation. Distillation under atmospheric pressure gives colorless liquid product A. GCMS analysis shows that it contains 17 grams of methyl formate and 5.5 grams of methyl acetate. The brown color liquid left weighs 115 grams with a heat of combustion 37.8 KJ/g. GCMS analysis shows that it is a mixture of aliphatic esters and aromatics. It contains 48 grams of methyl lactate, 19 grams of methyl glycolate, about 8 grams of fat acid esters (C15-C21), and about 30 grams of aromatics with boiling points ranging from 200 degrees Celsius to about 400 degrees Celsius. $^1$H-NMR of this aromatic product shows that the ratio of aliphatic hydrogen to aromatic hydrogen is 4.8:1 (FIG. 3), a ratio of the current diesels. The product yield is 101% based on the organic MSW.

Example 2

To a 1 liter stainless steel autoclave equipped with mechanical stirrer, add 750 ml of distilled water, 112 g of dried organic MSW B, 42 g of calcium oxide, and 1 g of anthraquinone. The autoclave is sealed, purged with nitrogen three times, then filled with nitrogen at a pressure of 0.2-1 MPa, heated to 180° C. and maintain at this temperature for ten minutes. The temperature is then increased to 250° C. and stirred at this temperature for 50 min. After cooling to a temperature below 50° C., a brown color liquid mixture is obtained (the color slowly turns deeper after the mixture is exposed to air). The liquid mixture is then cooled down to a temperature below 10 degrees Celsius with stirring. Pressed filtration is carried out with the temperature controlled below 10 degrees Celsius. A brown color solid product obtained is 218 grams with 28% of water content. The yield is 101% based on the organic MSW.

The brown color solid is dried under a vacuum with the temperature controlled below 60 degrees Celsius, then suspended in 1000 ml of anhydrous methanol, 100 g of dimethyl carbonate is added to the mixture. The mixture is sealed inside a 2 liter stainless steel autoclave equipped with mechanical stirrer. The reaction mixture is then heated to 180 degrees Celsius with vigorous stirring. After a two hour reaction, the reaction mixture is cooled down to room temperature. Pressed filtration is carried out to remove all solids. Products are isolated using distillation. Distillation under atmospheric pressure gives a colorless liquid product A. GCMS analysis shows that it contains 18 grams of methyl formate and 4.3 grams of methyl acetate. The brown color liquid left weights 114 grams with a heat of combustion 37.7 KJ/g. GCMS analysis shows that it is a mixture of aliphatic esters and aromatics. It contains 47 grams of methyl lactate, 19 grams of methyl glycolate, about 8 grams of fat acid esters (C15-C21), and about 30 grams of aromatics with boiling points ranging from 200 degrees Celsius to about 400 degrees Celsius. The product yield is 101% based on the organic MSW.

The results show that 9,10-dihydroxyanthracene and anthraquinone are both good catalysts for the reaction.

Example 3

To a 1 liter stainless steel autoclave equipped with mechanical stirrer, add 750 ml of distilled water, 112 g of dried organic MSW B, and 42 g of calcium oxide. The autoclave is sealed, purged with nitrogen three times, then filled with nitrogen at a pressure of 0.2-1 MPa, heated to 180° C. and maintain at this temperature for ten minutes. The temperature is then increased to 250° C. and stirred at this temperature for 50 min. After cooling to a temperature below 50° C., a black color sticky mixture is obtained. The mixture is then cooled down to a temperature below 10 degrees Celsius with stirring. Pressed filtration is carried out with the temperature controlled below 10 degrees Celsius. The black color solid product obtained is 120 grams with 35% of water content. The yield is 32% based on the organic MSW.

The result shows that the yield of liquid product is very low without catalyst.

Example 4

To a 1 liter stainless steel autoclave equipped with mechanical stirrer, add 750 ml of distilled water, 112 g of organic MSW A, 63 g of calcium oxide, and 1 g of 9,10-dihydroxyanthracene. The autoclave is sealed, purged with nitrogen three times, then filled with nitrogen at a pressure of 0.2-1 MPa, heated to 180° C. and maintain at this temperature for ten minutes. The temperature is then increased to 250° C. and stirred at this temperature for 50 min. After cooling to a temperature below 50° C., a brown color liquid mixture is obtained (the color slowly turns deeper after the mixture is exposed to air). The liquid mixture is then cooled down to a temperature below 10 degrees Celsius with stirring. Pressed filtration is carried out with the temperature controlled below 10 degrees Celsius. The brown color solid product obtained is 235 grams with 25% of water content. The yield is 101% based on the organic MSW.

The brown color solid is dried under a vacuum with the temperature controlled below 60 degrees Celsius, then suspended in 1000 ml of anhydrous methanol, 100 g of dimethyl carbonate is added to the mixture. The mixture is sealed inside a 2 liter stainless steel autoclave equipped with mechanical stirrer. The reaction mixture is then heated to 180 degree of Celsius with vigorous stirring. After a two hour reaction, the reaction mixture is cooled down to room temperature. Pressed filtration is carried out to remove all solids. Products are isolated using distillation. Distillation under atmospheric pressure gives colorless liquid product A. GCMS analysis shows that it contains 20 grams of methyl formate and 3.3 grams of methyl acetate. The brown color liquid left weighs 111 grams with a heat of combustion 37.5 KJ/g. GCMS analysis shows that it is a mixture of aliphatic esters and aromatics. It contains 58 grams of methyl lactate, 17 grams of methyl glycolate, about 7 grams of fat acid esters (C15-C23), and about 13.3 grams of aromatics with boiling points ranging from 200 degrees Celsius to about 400 degrees Celsius.

Example 5

Municipal Solid Waste is obtained from San Diego area of California. All visible plastic materials are hand-picked out before windblown sorting. The organic materials of MSW is isolated and analyzed their lignin content. These organic MSW has 11% lignin content and 29% ash content.

To a 1 liter stainless steel autoclave equipped with mechanical stirrer, add 750 ml of distilled water, 158 g of dried organic MSW, 42 g of calcium oxide, and 1 g of 9,10-dihydroxyanthracene. The autoclave is sealed, purged with nitrogen three times, then filled with nitrogen at a pressure of 0.2-1 MPa, heated to 180° C. and maintain at this temperature for ten minutes. The temperature is then increased to 250° C. and stirred at this temperature for 50 min. After cooling to a temperature below 50° C., a brown color liquid mixture is obtained (the color slowly turns deeper after the mixture is exposed to air). The liquid mixture is then cooled down to a temperature below 10 degrees Celsius with stirring. Pressed filtration is carried out with the temperature controlled below 10 degrees Celsius. The brown color solid product obtained is 268 grams with 23% of water content and 31% of ash content. The yield is 101% based on the organic MSW.

The brown color solid is dried under a vacuum with the temperature controlled below 60 degrees Celsius, then suspended in 1000 ml of anhydrous methanol, 100 g of dimethyl carbonate is added to the mixture. The mixture is sealed inside a 2 liter stainless steel autoclave equipped with mechanical stirrer. The reaction mixture is then heated to 180 degrees Celsius with vigorous stirring. After a two hour reaction, the reaction mixture is cooled down to room temperature. Pressed filtration is carried out to remove all solids. Products are isolated using distillation. Distillation under atmospheric pressure gives colorless liquid product A. GCMS analysis shows that it contains 20 grams of methyl formate and 3.8 grams of methyl acetate. The brown color liquid left weighs 111.3 grams with a heat of combustion 37.1 KJ/g. GCMS analysis shows that it is a mixture of aliphatic esters and aromatics. It contains 56 grams of methyl lactate, 18 grams of methyl glycolate, about 6 grams of fat acid esters (C15-C23), and about 18.3 grams of aromatics with boiling points ranging from 200 degrees Celsius to about 400 degrees Celsius. The product yield is 103% based on the organic MSW.

Example 6

Municipal Solid Waste is obtained from San Diego area of California. All visible plastic materials are hand-picked out before windblown sorting. The organic materials of MSW is isolated and analyzed their lignin content. These organic MSW has 11% lignin content and 29% ash content.

To a 1 liter stainless steel autoclave equipped with mechanical stirrer, add 750 ml of distilled water, 158 g of dried organic MSW, 42 g of calcium oxide, and 1 g of anthraquinone. The autoclave is sealed, purged with nitrogen three times, then filled with nitrogen at a pressure of 0.2-1 MPa, heated to 180° C. and maintain at this temperature for ten minutes. The temperature is then increased to 250° C. and stirred at this temperature for 50 min. After cooling to a temperature below 50° C., a brown color liquid mixture is obtained (the color slowly turns deeper after the mixture is exposed to air). The liquid mixture is then cooled down to a temperature below 10 degrees Celsius with stirring. Pressed filtration is carried out with the temperature controlled below 10 degrees Celsius. The brown color solid product obtained is 277 grams with 23.6% of water content and 31% of ash content. The yield is 101% based on the organic MSW.

The brown color solid is dried under a vacuum with the temperature controlled below 60 degrees Celsius, then suspended in 1000 ml of anhydrous methanol, 100 g of dimethyl carbonate is added to the mixture. The mixture is sealed inside a 2 liter stainless steel autoclave equipped with mechanical stirrer. The reaction mixture is then heated to 180 degrees Celsius with vigorous stirring. After a two hour reaction, the reaction mixture is cooled down to room temperature. Pressed filtration is carried out to remove all solids. Products are isolated using distillation. Distillation under atmospheric pressure gives colorless liquid product A. GCMS analysis shows that it contains 19 grams of methyl formate and 4.5 grams of methyl acetate. The brown color liquid left weighs 110.1 grams with a heat of combustion 37.5 KJ/g. GCMS analysis shows that it is a mixture of aliphatic esters and aromatics. It contains 54 grams of methyl lactate, 19 grams of methyl glycolate, about 6 grams of fat acid esters (C15-C23), and about 18.5 grams of aromatics with boiling points ranging from 200 degrees Celsius to about 400 degrees Celsius. The product yield is 103% based on the organic MSW. This result confirms that anthraquinone and 9,10-dihydroxyanthracene are both good catalyst for the hydrolysis reaction.

Several other catalysts are also tested using the procedure described in Example 5, and very similar results are obtained using these catalysts, such as 1-nitro-9,10-dihydroxyanthracene, sodium anthraquinone-2-sulfonate, sodium 9,10-dihydroxyanthracene-1-sulfonate, and dinitro-9,10-dihydroxyanthracene.

Example 7

Municipal Solid Waste is obtained from San Diego area of California. All visible plastic materials are hand-picked out before windblown sorting. The organic materials of MSW is isolated and analyzed their lignin content. These organic MSW has 11% lignin content and 29% ash content.

To a 1 liter stainless steel autoclave equipped with mechanical stirrer, add 750 ml of distilled water, 158 g of dried organic MSW, 42 g of calcium oxide, and 1 g of anthraquinone. The autoclave is sealed, purged with nitrogen three times, then filled with nitrogen at a pressure of 0.2-1 MPa, heated to 180° C. and maintain at this temperature for ten minutes. The temperature is then increased to 250° C. and stirred at this temperature for 50 min. After cooling to a temperature about 80° C., a brown color liquid mixture is obtained (the color slowly turns deeper after the mixture is exposed to air). Pressed filtration is carried out with the temperature controlled higher than 60 degrees Celsius, a brown color solid product M obtained is 50.2 grams with 24% of water and 30% of ash. The yield is about 127% based on the lignin content of the MSW. The liquid solution is then cooled down to a temperature below 10 degrees Celsius with stirring. Pressed filtration is carried out with the temperature controlled below 10 degrees Celsius. The brown color solid product obtained is 228 grams with 23.6% of water content and 31% of ash content. The yield is 101% based on the organic MSW.

The brown color solid product M is dried under a vacuum with the temperature controlled below 60 degrees Celsius, then suspended in 120 ml of anhydrous methanol, 10 g of dimethyl carbonate is added to the mixture. The mixture is sealed inside a 200 ml stainless steel autoclave equipped with mechanical stirrer. The reaction mixture is then heated to 180 degrees Celsius with vigorous stirring. After a two hour reaction, the reaction mixture is cooled down to room temperature. Pressed filtration is carried out to remove all solids. Solvent and unreacted dimethyl carbonate are distilled out first, then the desired products are isolated using molecular distillation. The light brown color liquid product weighs 25.1 grams with a heat of combustion 46.9 KJ/g. GCMS analysis shows that it is a mixture of aliphatic esters and aromatics. It has about 6 grams of fat acid esters (C15-C23), and about 19.1 grams of aromatics with boiling points ranging from 200 degrees Celsius to about 400 degrees Celsius.

Example 8

Municipal Solid Waste is obtained from San Diego area of California. All visible plastic materials are hand-picked out before windblown sorting. The organic materials of MSW is isolated and analyzed their lignin content. These organic MSW has 11% lignin content and 29% ash content.

To a 1 liter stainless steel autoclave equipped with mechanical stirrer, add 750 ml of distilled water, 158 g of dried organic MSW, 42 g of calcium oxide, and 5 g of product M obtained in Example 7. The autoclave is sealed, purged with nitrogen three times, then filled with nitrogen at a pressure of 0.2-1 MPa, heated to 180° C. and maintain at this temperature for ten minutes. The temperature is then increased to 250° C. and stirred at this temperature for 50 min. After cooling to a temperature below 50° C., a brown color liquid mixture is obtained (the color slowly turns deeper after the mixture is exposed to air). The liquid mixture is then cooled down to a temperature below 10 degrees Celsius with stirring. Pressed filtration is carried out with the temperature controlled below 10 degrees Celsius. The brown color solid product obtained is 284 grams with 23.7% of water content and 31% of ash content. The yield is 101% based on the organic MSW.

The brown color solid is dried under a vacuum with the temperature controlled below 60 degrees Celsius, then suspended in 1000 ml of anhydrous methanol, 100 g of dimethyl carbonate is added to the mixture. The mixture is sealed inside a 2 liter stainless steel autoclave equipped with mechanical stirrer. The reaction mixture is then heated to 180 degrees Celsius with vigorous stirring. After a two hour reaction, the reaction mixture is cooled down to room temperature. Pressed filtration is carried out to remove all solids. Products are isolated using distillation. Distillation under atmospheric pressure gives colorless liquid product A. GCMS analysis shows that it contains 19 grams of methyl formate and 4.5 grams of methyl acetate. The brown color liquid left weighs 111.6 grams with a heat of combustion 37.5 KJ/g. GCMS analysis shows that it is a mixture of aliphatic esters and aromatics. It contains 55 grams of methyl lactate, 19 grams of methyl glycolate, about 6 grams of fat acid esters (C15-C23), and about 18.8 grams of aromatics with boiling points ranging from 200 degrees Celsius to about 400 degrees Celsius. The product yield is 103% based on the organic MSW.

This result show that the aromatic product (product M) obtained from the hydrolysis of organic MSW is good catalyst for the hydrolysis of organic MSW.

Example 9

Municipal Solid Waste is obtained from the San Diego area of California. Windblown sorting is used to obtain the organic materials of MSW. The contents of organic MSW are analyzed and the result shows that these organic MSW have 10% lignin content, 10% plastics content, and 29% ash content.

To a 1 liter stainless steel autoclave equipped with mechanical stirrer, add 750 ml of distilled water, 158 g of dried organic MSW, 42 g of calcium oxide, and 1 g of 9,10-dihydroxyanthracene. The autoclave is sealed, purged with nitrogen three times, then filled with nitrogen at a pressure of 0.2-1 MPa, heated to 180° C. and maintain at this temperature for ten minutes. The temperature is then increased to 250° C. and stirred at this temperature for 50 min. After cooling to a temperature below 50° C., a brown color liquid mixture is obtained (the color slowly turns deeper after the mixture is exposed to air). The liquid mixture is then cooled down to a temperature below 10 degrees Celsius with stirring. Pressed filtration is carried out with the temperature controlled below 10 degrees Celsius. The brown color solid product obtained is 271 grams with 23% of water content and 31% of ash content. The yield is 101% based on the organic MSW.

The brown color solid is dried under a vacuum with the temperature controlled below 60 degrees Celsius, then suspended in 1000 ml of anhydrous methanol, 100 g of dimethyl carbonate is added to the mixture. The mixture is sealed inside a 2 liter stainless steel autoclave equipped with mechanical stirrer. The reaction mixture is then heated to 180 degrees Celsius with vigorous stirring. After a two hour reaction, the reaction mixture is cooled down to room temperature. Pressed filtration is carried out to remove all solids. Analysis shows that this solid contains about 9 grams of plastics. Liquid products are isolated using distillation. Distillation under atmospheric pressure gives colorless liquid product A. GCMS analysis shows that it contains 18 grams of methyl formate and 3.3 grams of methyl acetate. The brown color liquid left weighs 102.5 grams with a heat of combustion 36.3 KJ/g. GCMS analysis shows that it is a mixture of aliphatic esters and aromatics. It contains 51 grams of methyl lactate, 15 grams of methyl glycolate, about 5 grams of fat acid esters (C15-C23), and about 18.1 grams of aromatics with boiling points ranging from 200 degrees Celsius to about 400 degrees Celsius. The product yield is 103% based on the organic MSW.

This result shows that plastics in MSW do not need to be separated before hydrolysis.

The invention claimed is:
1. A process for converting organic Municipal Solid Waste (MSW) into liquid fuels or chemical products in quantitative yield via a catalytic one-pot hydrolytic depolymerization of the organic MSW, comprising the steps of:
  (a) providing the organic MSW;
  (b) subjecting the organic MSW to a catalytic one-pot hydrolytic depolymerization in the presence of a catalyst and an alkaline earth metal oxide or hydroxide or a transition metal oxide or hydroxide; wherein the catalyst is an organic chemical of formula I or II:

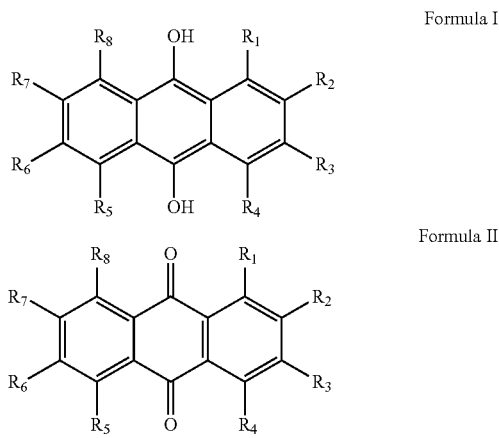

wherein in formula I and formula II, $R_1$, $R_2$, $R_3$, $R_4$, $R_5$, $R_6$, $R_7$, and $R_8$ are the same or different, and are selected from H, $SO_3H$, $NO_2$, $NH_2$ and OH;
  (c) filtering out the depolymerization product of the organic MSW; and
  (d) alkylating the product of depolymerization.

2. The process according to claim 1 in which filtering out the depolymerization product of organic MSW occurs at a temperature below ten degrees Celsius.

3. The process according to claim 2 in which the organic MSW comprises paper, paperboard, food scraps, yard trimmings, rubber, leather, textiles, wood and plastics.

4. The process according to claim 1 in which the filtering is pressed filtration carried out at a temperature above 60 degrees Celsius wherein a brown color solid product is obtained.

5. The process according to claim 2 in which the metal oxides or hydroxides are selected from magnesium, calcium, strontium, barium, iron or copper.

6. The process according to claim 2 in which the ratio of organic MSW to oxide or hydroxide is in the range of 50 grams of organic MSW:1 molar equivalent of oxide or hydroxide anion to 100 grams of organic MSW:1 molar equivalent of oxide or hydroxide anion.

7. The process according to claim 2 in which the alkylation step produces liquid fuels.

8. The process according to claim 7 in which the alkylation step is a one step process and is performed using dimethyl sulfate or dimethyl carbonate as alkylation reagents.

9. The process of claim 7 wherein the liquid fuels are separated into aromatic and non-aromatic chemicals.

10. The process of claim 9 in which the aromatic chemicals are used as the catalysts.

* * * * *